US006780989B2

(12) United States Patent
Cole et al.

(10) Patent No.: US 6,780,989 B2
(45) Date of Patent: Aug. 24, 2004

(54) DIRIBONUCLEOSIDE PHOSPHORAMIDITES

(75) Inventors: Douglas L. Cole, San Diego, CA (US); Vasulinga Ravikumar, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/346,659

(22) Filed: Jan. 17, 2003

(65) Prior Publication Data

US 2003/0114662 A1 Jun. 19, 2003

Related U.S. Application Data

(63) Continuation of application No. 10/068,604, filed on Feb. 6, 2002, now abandoned, which is a continuation of application No. 09/756,354, filed on Jan. 8, 2001, now Pat. No. 6,403,781, which is a continuation of application No. 08/775,011, filed on Dec. 27, 1996, now Pat. No. 6,172,217.

(51) Int. Cl.$^7$ .............................................. C07H 21/02
(52) U.S. Cl. ..................................................... 536/26.5
(58) Field of Search ....................................... 536/26.5

(56) References Cited

U.S. PATENT DOCUMENTS

| | | |
|---|---|---|
| 3,687,808 A | 8/1972 | Merigan, Jr. et al. |
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,725,677 A | 2/1988 | Köster et al. |
| 4,973,679 A | 11/1990 | Caruthers et al. |
| 5,132,418 A | 7/1992 | Caruthers et al. |
| RE34,069 E | 9/1992 | Köster et al. .................. 536/27 |
| 5,151,510 A | 9/1992 | Stec et al. ...................... 536/27 |
| 5,166,387 A | 11/1992 | Hirschbein .................. 558/129 |
| 5,212,295 A | 5/1993 | Cook ......................... 536/26.7 |
| 5,292,875 A | 3/1994 | Stec et al. ................ 536/25.33 |
| 5,405,985 A | 4/1995 | Parker et al. ................ 556/427 |
| 5,436,331 A * | 7/1995 | Reese ......................... 536/55.3 |
| 5,506,212 A * | 4/1996 | Hoke et al. .................... 514/44 |
| 5,512,668 A * | 4/1996 | Stec et al. ................ 536/25.33 |
| 5,525,719 A * | 6/1996 | Srivastava et al. ......... 536/26.7 |
| 5,571,902 A * | 11/1996 | Ravikumar et al. ........ 536/22.1 |
| 5,635,488 A * | 6/1997 | Cook et al. .................... 514/44 |
| 5,672,697 A * | 9/1997 | Buhr et al. ................. 536/26.7 |
| 6,015,886 A * | 1/2000 | Dale et al. .................. 536/23.1 |
| 6,172,217 B1 * | 1/2001 | Cole et al. ................ 536/25.31 |
| 6,403,781 B2 * | 6/2002 | Cole et al. ................ 536/25.31 |

FOREIGN PATENT DOCUMENTS

| | | | |
|---|---|---|---|
| EP | 0339842 | * | 11/1989 |
| EP | 0386987 | * | 9/1990 |
| EP | 0710667 A2 | * | 5/1996 |
| JP | 7157498 | * | 6/1995 |
| WO | WO 91/06556 | | 5/1991 |
| WO | WO 91/10671 | | 7/1991 |
| WO | WO 93/13118 | | 7/1993 |
| WO | 9415946 | * | 7/1994 |
| WO | WO 95/26204 | | 10/1995 |
| WO | 9532980 | * | 12/1995 |
| WO | 9630386 | * | 3/1996 |
| WO | WO 2001/49701 A1 | * | 7/2001 |

OTHER PUBLICATIONS

Letsinger et al., "Cholesteryl–Conjugated Oligonucleotides: Synthesis, Properties, and Activity as Inhibitors of Replication of Human Immunodeficiency Virus in Cell Culture," *Proc. National Academy of Sciences USA*, 86, 6553–6556 (Sep., 1989).*

Stec et al.(II), "Stereochemical Studies of the Formation of Chiral Internucleotide Linkages by Phosphoramidite Coupling in the Synthesis of Oligodeoxyribonucleotides," *Tetrahedron Letters*, 25(46), 5279–5282 (1984).*

Marugg et al., "Synthesis of Phosphorothioate–Containing DNA Fragments by a Modified Hydroxybenzotriazole Phosphotriester Approach," *Nucleic Acids Research*, 12(23), 9095–9110 (Dec. 11, 1984).*

Stec et al. (III), "Automated Solid–Phase Synthesis, Separation, and Stereochemistry of Phosphorothioate Analogues of Oligodeoxyribonucleotides," *Journal American Chemical Society*, 106(20), 6077–6079 (Oct. 3, 1984).*

Stec et al. (IV), "Reversed–Phase High–Performance Liquid Chromatographic Separation of Diasteroisomeric Phosphorothioate Analogues of Oligodeoxyribonucleotides and Other Backbone–Modified Congeners of DNA," *Journal of Chromatography*, 326, 263–280 (Jun. 19, 1985).*

Stec et al. (V), "Synthesis and Absolute Configuration of P–Chiral O–Isopropyl Oligonucleotide Triesters," *Tetrahedron Letters*, 26(18), 2191–2194 (1985).*

Matsukura et al., "Phosphorothioate Analogs of Oligodeoxynucleotides: Inhibitors of Replication and Cytopathic Effects of Human Immunodeficiency Virus," *Proc. National Academy Sciences USA*, 84, 7706–7710 (Nov., 1987).*

Stein et al., "Phosphorothioate and Normal Oligodeoxyribonucleotides with 5'–Linked Acridine: Characterization and Preliminary Kinetics of Cellular Uptake," *Gene*, 72(1–2), 333–341 (Dec. 10, 1988).*

Roelen et al., "A Study on the Use of Phenylacetyl Disulfide in the Solid–Phase Synthesis of Oligodeoxynucleoside Phosphorothioates," *Recueil des Travaux Chimiques des Pays–Bas*, 110(7–8), 325–331 (Jul.–Aug., 1991).*

Charubala et al., "84. Nucleotides (Part XXXVI). Synthesis and Biological Characterization of Phosphorothioate Analogues of (3'–5') Adenylate Trimer," *Helvetica Chimica Acta*, 74(4), 892–898 (Jun. 19, 1991).*

(List continued on next page.)

*Primary Examiner*—James O. Wilson
*Assistant Examiner*—L E Crane
(74) *Attorney, Agent, or Firm*—Woodcock Washburn LLP

(57) ABSTRACT

This invention presents novel methods for synthesizing phosphorothioate oligonucleotides, using support-bound phosphoramidites. Novel intermediates useful in the methods are also provided.

7 Claims, No Drawings

OTHER PUBLICATIONS

Routledge et al., "A New Deprotection Strategy for Automated Oligonucleotide Synthesis Using a Novel Silyl–Linked Solid Support," *Bioorganic & Medicinal Chemistry Letters*, 5(18), 2059–2064 (Sep. 21, 1995).*

Ravikumar et al. (II), "2–Diphenylmethylsilyl (DPSE): A Versatile Protecting Group for Oligodeoxyribonucleotide Synthesis," *Gene*, 149(1), 157–161 (Nov. 4, 1994).*

Usman et al., "Automated Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethionine tRNA," *Journal American Chemical Society*, 109(25), 7845–7854 (1987).*

Manoharan et al., "A 2'–O –Thiol Tether in the Ribose Moiety of Nucleic Acids for Conjugation Chemistry," *Gene*, 149(1), 147–156 (Nov. 4, 1994).*

Wyrzykiewicz et al., "Stereo–Reproducibility of the Phosphoramidite Method in the Synthesis of Oligonucleotide Phosphorothioates," *Bioorganic Chemistry*, 23(1), 33–41 (Mar., 1995).*

Ravikumar et al. (III), "Use of 2–Diphenylmethysilyl (DPSE) Protecting Group in Oligodeoxyribonucleotide Synthesis Via Phosphoroamidite Approach," *Bioorganic & Medicinal Chemistry Letters*, 3(12), 2637–2640 (Dec., 1993).*

Lesnikowski et al.(I), "Octa(Thymidine Methanephosphonates) of Partially Defined Stereochemistry: Synthesis and Effect of Chirality at Phosphorus on Binding to Pentadecadeoxyriboadenylic Acid," *Nucleic Acids Research*, 18(8), 2109–2115 (1990).*

Lesnikowski et al.(II), "Stereoselective Synthesis of P–Homochiral Oligo(Thymidine Methanephosphonates)," *Nucleic Acids Research*, 16(24), 11675–11689 (Dec., 1988).*

M. H. Caruthers, "DNA Synthesis for Nonchemists: The Phosphoramidite Method on Silica Supports," Chapter 3 in *Synthesis and Applications of DNA and RNA*, S. A. Narang (ed.), Academic Press, Inc., New York, NY, 1987, only pp. 47–94 supplied.*

Cheruvallath, Z.S., et al., "Sulfurization efficiency in the solution phase synthesis of deoxyribonucleoside phosphorothioates—comparison of sulfur triethylamine with various sulfurizing agents," *Nucleosides & Nucleotides*, 1996, 15(9), 1441–1445.

Ravikumar, V.T.,et al., "4–cyano–2–butenyl group: a new type of protecting group in oligonucleotide synthesis via phosphoramidite approach," *Tetrahedron Letters*, 1996, 37(37), 6643–6646.

Alul et al., "Oxalyl–CPG: a labile support for synthesis of sensitive oligonucleotide derivatives", *Nucl. Acids. Res.*, 1991, 19(7), 1527–1532.

Beaucage et al., "Advances in the Synthesis of Oligonucleotides by the Phosphoramidite Approach", *Tetra.*, 1992, 48(12), 2223–2311.

Berner et al., "Studies on the role of tetrazole in the activation of phosphoramidites", *Nucl. Acids Res.*, 1989, 17(3), 853–864.

Brown et al., "Modern machine–aided methods of oligodeoxyribonucleotide synthesis", *Oligonucleotide and Analogs: A Practical Approach*, Eckstein, F. (ed.), 1991, IRL Press, 1–24.

Cook, "Medicinal chemistry of antisense oligonucleotides—future opportunities", *Anti–Cancer Drug Design*, 1991, 6, 585–607.

Dahl et al., "Mechanistic studies on the phosphoramidite coupling reaction in oligonucleotide synthesis. I. Evidence for nucleophilic catalysis by tetrazole and rate variations with the phosphorus substituents",*Nucl. Acids Res.*, 1987, 15(4), 1729–1743.

Delgardo et al., "The Uses and Properties of PEG–Linked Proteins", *Critical Rev. in Therapeutic Drug Carrier Systems*, 1992, 9(3,4), 249–304.

Efimov et al., "New efficient sulfurizing reagents for the preparation of oligodeoxyribonucleotide phosphorothioate analogues", *Nucl. Acids Res.*, 1995, 23(20), 4029–4033.

Englisch et al., "Chemically Modified Oligonucleotides as Probes and Inhibitors", *Angew. Chem. Int. Ed. Engl.*, 1991, 30(6), 613–629 (Jun., 1991).

Grandas et al., "Synthesis of Deoxycytidine Oligomers Containing Phosphorodithioate Linkages", *Tetra. Lett.*, 1989, 30(5), 543–546.

Iyer, R. et al, "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.* 1990, 112, 1253–1254.

Iyer, R. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.*. 1990, 55(15), 4693–4699.

Kamer, P. et al., "An Efficient Approach Toward the Synthesis of Phosphorothioate Diesters via the Schonberg Reaction", *Tetrahedron Letters* 1989, 30(48), 6757–6760.

Kroschwitz, J.I. (ed.), *Concise Encyclopedia of Polymer Science and Engineering*, John Wiley & Sons, 1990, 858–859.

Nielsen et al., "Synthesis and Characterization of Dinucleoside Phosphorodithioates", *Tetra. Lett.*, 1988, 29(24), 2911–2914.

Nielson et al., "Thermal Instability of Some Alkyl Phosphorodiamides", *J. Chem. Res.*, 1986, 26–27.

Ouchi et al., "Synthesis and Antitumor Activity of Poly(Ethylene Glycol)s Linked to 5–Fluorouracil Via a Urethane or Urea Bond", *Drug Design and Discovery*, 1992, 9, 93–105.

Rao, M.V. et al. "Dibenzoyl Tetrasulphide—A Rapid Sulphur Transfer Agent in the Synthesis of Phosphorothioate Analogues of Oligonucleotides",*Tetra. Lett.*, 1992, 33(33), 4839–4842.

Ravasio et al., "Selective Hydrogenations Promoted by Copper Catalysis. 1. Chemoselectivity, Regioselectivity, and Stereoselectivity in the Hydrogenation of 3–Substituted Steroids", *J. Org. Chem.*, 1991, 56, 4329–4333.

Secrist et al., Absract 21, Program and Abstracts, Tenth International Roundtable, Nucleosides, Nucleotides and their Biological Applications, Park City, Utah, Sep. 16–20, 1992.

Sanghvi, *Antisense Research and Application*, S.T. Crooke and B. Lebleu (eds.), CRC Press, Chapter 15, 1993.

Uhlmann et al., "Antisense Oligonucleotides: A New Therapeutic Principle", *Chem. Rev.*, 1990, 90(4), 543–584 (Jun., 1990).

Uznanski et al., "Deoxyribonucleoside 3'–Phosphordiamidites as Substrates for Solid Supported Synthesis of Oligodeoxyribonucleotides and Their Phosphorothioate and DNA–Triester Analogues", *Tetra. Lett.*, 1987, 28, 3401–3404.

Vu, H. et al., "Internucleotide Phosphite Sulfurization with Tetraethylthiuram Disulfide. Phosphorothioate Oligonucleotide Synthesis via Phosphoramidite Chemistry", *Tetrahedron Letters* 1991, 32(26), 3005–3008.

Wright, P. et al., "Large Scale Synthesis of Oligonucleotides via Phosphoramidite Nucleosides and a High–loaded Polystyrene Support", *Tetrahedron Letters* 1993, 34(21), 3373–3376.

Xu et al., "Efficient introduction of phosphorothioates into RNA oligonucleotides by 3–ethoxy–1,2, 4–dithiazoline–5–one (EDITH)", *Nucl. Acids Res.*, 1996, 24(18), 3643–3644.

Xu et al., "Use of 1,2,4–dithiazolidine–3,5–dione (DtsNH) and 3–ethoxy–1,2,4–dithiazoline–5–one (EDITH) for synthesis of phosphorothioate–containing oligodeoxyribonucleotides", *Nucl. Acids Res.*, 1996, 24(9), 1602–1607.

Yamana et al., "A Simple Preparation of 5'–Dimethoxytrityl Deoxyribonucleoside 3'–O–Phosphorbisdiethylamidites as Useful Intermediates in the Synthesis of Oligodeoxyribonucleotides and Their Phosphorodiethylamidate Analogs on a Solid Support", *Tetrahedron*, 1989, 45913), 4135–4140.

Zon et al., "Phosphorothioate oligonucleotides", *Oligonucleotide and Analogs: A Practical Approach*, Eckstein, F. (ed.), 1991, IRL Press, 87–103.

Manoharan et al., "Novel Functionalization of the Sugar Moiety of Nucleic Acids for Multiple Labeling in the Minor Groove," *Tetrahedron Letters*, 1991, 32, 7171–7174.

Martin, von P., "Ein neuer Zugang zu 2'–O–Alkylribonucleosiden und Eigenschaften deren Oligonucleotide," *Helvetica Chemica Acta*, 1995, 78, 486–504(Mar. 22, 1995).

Marugg, J. E. et al., "A New and Verstile Approach to the Preparation of Valuable Deoxynucleoside 3'–Phosphite Intermediates," *Tetrahedron Letters*, 1986, 27(20), 2271–2274.

\* cited by examiner

DIRIBONUCLEOSIDE PHOSPHORAMIDITES

This Application is a continuation of application Ser. No. 10/068,604 filed Feb. 6, 2002, now abandoned, which is a continuation of application Ser. No. 09/756,354 filed Jan. 8, 2001, now U.S. Pat. No. 6,403,781, which is a continuation of Ser. No. 08/775,011 filed Dec. 27, 1996, now U.S. Pat. No. 6,172,217.

FIELD OF THE INVENTION

This invention is directed to methods for synthesis of phosphorothioate oligonucleotides and to novel synthetic intermediates useful in the methods. The methods comprise the in-situ generation of amidites on a solid support. The methods are useful, inter alia, for the preparation of phosphorothioate oligonucleotides which, in turn, are useful as diagnostic reagents, research reagents and therapeutics agents.

BACKGROUND OF THE INVENTION

It is well known that most of the bodily states in mammals, including most disease states, are affected by proteins. Such proteins, either acting directly or through their enzymatic functions, contribute in major proportion to many diseases in animals and man. Classical therapeutics has generally focused on interactions with such proteins in efforts to moderate their disease causing or disease potentiating functions. Recently, however, attempts have been made to moderate the actual production of such proteins by interactions with molecules that direct their synthesis, such as intracellular RNA. By interfering with the production of proteins, it has been hoped to affect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another.

Prior attempts at antisense therapy have provided oligonucleotides or oligonucleotide analogs that are designed to bind in a specific fashion to a specific mRNA by hybridization (i.e., oligonucleotides that are specifically hybridizable with a target mRNA). Such oligonucleotides and oligonucleotide analogs are intended to inhibit the activity of the selected mRNA by any of a number of mechanisms, i.e., to interfere with translation reactions by which proteins coded by the mRNA are produced. The inhibition of the formation of the specific proteins that are coded for by the mRNA sequences interfered with have been hoped to lead to therapeutic benefits; however there are still problems to be solved. See generally, Cook, P. D. *Anti-Cancer Drug Design* 1991, 6, 585; Cook, P. D. *Medicinal Chemistry Strategies for Antisense Research, in Antisense Research & Applications*, Crooke, et al., CRC Press, Inc.; Boca Raton, Fla., 1993; Uhlmann, et al., *A. Chem. Rev.* 1990, 90, 543.

Oligonucleotides and oligonucleotide analogs are now accepted as therapeutic agents holding great promise for therapeutics and diagnostics methods. But applications of oligonucleotides and oligonucleotide analogs as antisense agents for therapeutic purposes, diagnostic purposes, and research reagents often require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides and oligonucleotide analogs toward nuclease degradation.

A serious deficiency of unmodified oligonucleotides for these purposes, particularly antisense therapeutics, is the enzymatic degradation of the administered oligonucleotides by a variety of intracellular and extracellular ubiquitous nucleolytic enzymes.

A number of chemical modifications have been introduced into antisense agents (i.e., oligonucleotides and oligonucleotide analogs) to increase their therapeutic activity. Such modifications are designed to increase cell penetration of the antisense agents, to stabilize the antisense agents from nucleases and other enzymes that degrade or interfere with their structure or activity in the body, to enhance the antisense agents' binding to targeted RNA, to provide a mode of disruption (terminating event) once the antisense agents are sequence-specifically bound to targeted RNA, and to improve the antisense agents' pharmacokinetic and pharmacodynamic properties. It is unlikely that unmodified, "wild type," oligonucleotides will be useful therapeutic agents because they are rapidly degraded by nucleases.

Oligonucleotides which have been modified to contain phosphorothioate linkages are capable of terminating RNA by activation of RNase H upon hybridization to RNA. These oligonucleotide analogs have been demonstrated to be sequence specific regulators of gene expression in eukaryotic and procaryotic systems, and are the most promising candidates to date for practical application as "antisense" therapeutic agents. See Eckstein, *Oligonucleotide and Analogs, A Practical Approach*, 1991, IRL Press, pp. 87–103.

Potential applications of phosphorothioate oligonucleotides as drugs have created a new challenges in the large-scale synthesis of these compounds. Thus, there remains a need for improved methods of synthesizing phosphorothioate oligonucleotides. The present invention addresses these, as well as other needs.

SUMMARY OF THE INVENTION

The present invention is directed to novel methods for the preparation of oligomeric compounds having phosphorothioate linkages. The present invention discloses solid support oligonucleotide synthetic methods which involve the generation of support-bound phosphoramidites. In preferred embodiments, the methods comprise the steps of:

reacting a phosphordiamidite of formula:

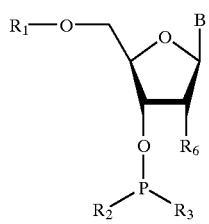

wherein:

- $R_1$ is a protecting group;
- $R_2$ and $R_3$ are dialkylamino or morpholino;
- B is a nucleosidic base; and
- $R_6$ is halogen, O-alkyl, O-alkylamino, O-alkylalkoxy, protected O-alkylamino, O-alkylaminoalkyl, O-alkyl imidazole, or a polyether of the formula (O-alkyl)$_m$, where m is 1 to about 10;

with a support-bound synthon of formula:

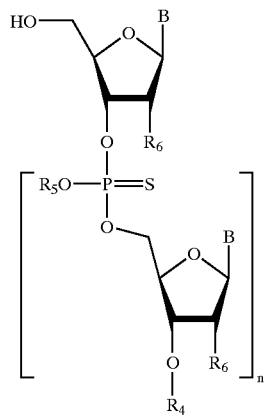

wherein:

- $R_4$ is a linker connected to a solid support;
- $R_5$ is a phosphoryl protecting group; and
- n is 0 to 100;

to form a support-bound phosphoramidite. The support-bound phosphoramidite has the formula:

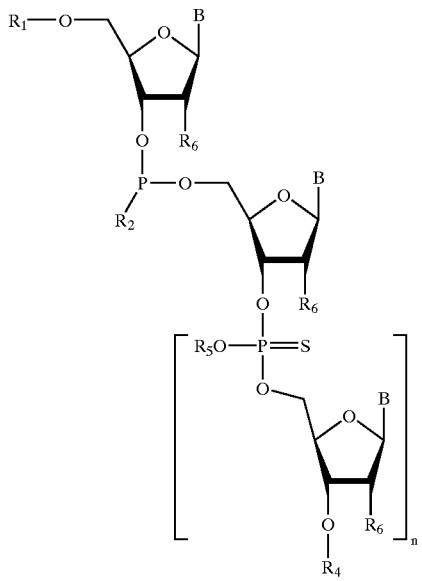

The support-bound phosphoramidite is protected, preferably by reaction with a reagent of formula $R^5$—OH, to form a support-bound phosphite of formula:

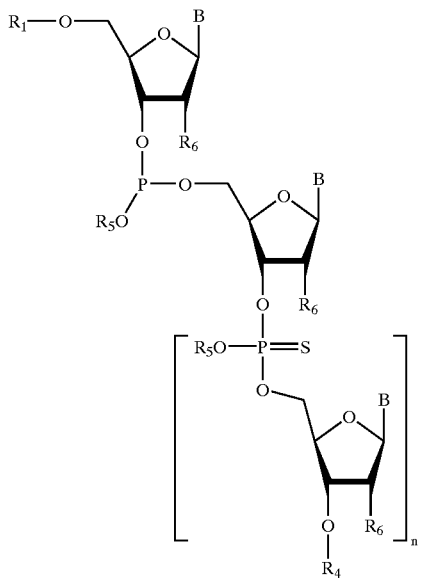

The support-bound phosphite is then sulfurized to form a protected phosphorothioate, and then the protected phosphorothioate is deprotected to form a further support-bound synthon wherein n is increased by 1.

Throughout, it is understood that variable substituents $R_{1-6}$ may be the same or different in differing oligomeric subunits.

In some preferred embodiments, $R_2$ and $R_3$ are diisopropylamino. In other preferred embodiments $R_5$ is 2-cyanoethyl, 4-cyano-2-butenyl, or diphenylmethylsilylethyl. In further preferred embodiments the reaction of the phosphite compound with the support-bound synthon is preformed in the presence of an organic base, preferably tetrazole. In other preferred embodiments the support-bound phosphite is oxidized with a sulfurization reagent such as Beaucage reagent, tetraethylthiuram disulfide, dibenzoyl tetrasulfide, phenacetyl disulfide, 1,2,4-dithiuazoline-5-one, 3-ethoxy-1,2,4-dithiuazoline-5-one, a disulfide of a sulfonic acid, sulfur, or sulfur in combination with a ligand such as triaryl, trialkyl, triaralkyl, or trialkaryl phosphines.

The present methods provide for the synthesis of oligonucleotides consisting of a wide variety of nucleosidic bases, including naturally occurring nucleosidic bases such as adenine, guanine, thymine, cytosine, and uracil, as well as nonnaturally occurring nucleobases.

In preferred embodiments n is from 0 to about 100, preferably 1 to about 30 and more preferably 15 to about 25.

The invention also provides compounds of the formula:

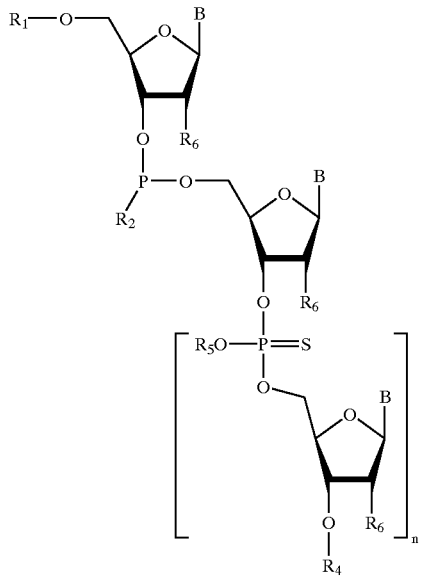

wherein:
B, $R_1$, $R_2$, $R_4$, $R_5$, and $R_6$ are as defined above, and n is 1 to about 100.

DETAILED DESCRIPTION OF PREFERRED EMBODIMENTS

The present invention presents novel methods for the synthesis of phosphorothioate oligonucleotides, which comprise the "in-situ" generation of a phosphoramidite bound to a solid support. In preferred embodiments of the invention a phosphordiamidite compound of formula:

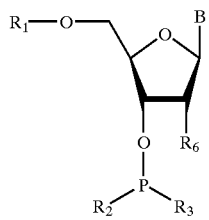

wherein:
$R_1$ is a protecting group;
B is a nucleosidic base;
$R_2$ and $R_3$ are dialkylamino or morpholino; and
$R_6$ is halogen, O-alkyl, O-alkylamino, O-alkylalkoxy, protected O-alkylamino, O-alkylaminoalkyl, O-alkyl imidazole, or a polyether of the formula (O-alkyl)$_m$, where m is 1 to about 10;

is reacted with a support-bound synthon of formula:

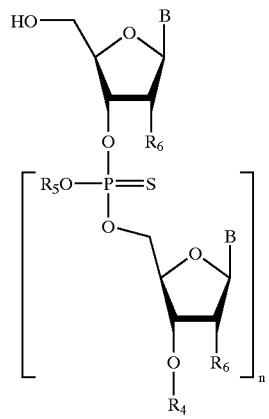

wherein:
$R_4$ is a linker connected to a solid support;
$R_5$ is a phosphoryl protecting group;
n is 0 to about 100;
to form a support-bound phosphoramidite of formula:

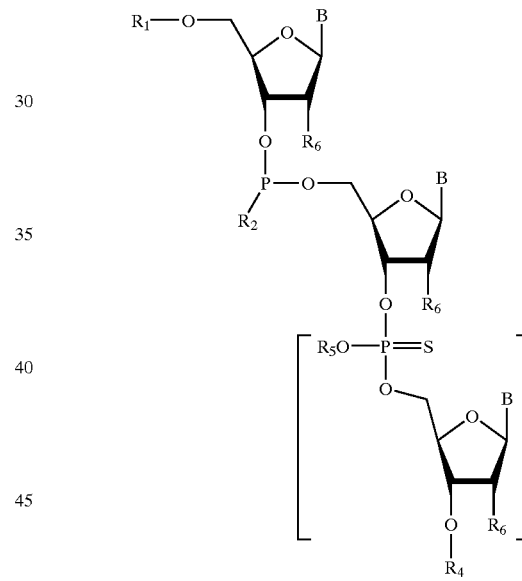

Phosphorodiamidites can be prepared, for example, by the condensation of a bis(dialkylamino)chlorophosphine with a 5'-protected nucleoside according to the procedure of Uznanski et al., *Tetrahedron Letters* 1989 30 (5) 543–546.

In preferred embodiments of the methods of the present invention, the initial support-bound synthon is prepared by the covalent attachment of an appropriately protected nucleoside to a solid support through the nucleoside 3'-oxygen, preferably through a linker molecule, according to known procedures. See, for example, Eckstein, supra. Procedures for the protection of nucleoside 5'-hydroxyls, exocyclic amine groups, and other functionalities can be found, for example, in Greene and Wuts, *Protective Groups in Organic Synthesis*, 2d ed, John Wiley & Sons, New York, 1991. The 5'-O-protecting group of the support linked nucleoside is typically removed by treatment with dilute acid and washed (rinsed) from the support with a solvent, preferably anhydrous acetonitrile. The reaction of phosphordiamidite and support-bound synthon is then performed in a solvent such as acetonitrile, preferably in the presence of an activating agent which is typically an organic base such as, for example, tetrazole. The resulting support-bound amidite is protected by the addition of a phosphoryl protecting group. Phosphoryl protecting groups are known in the art as protecting groups suitable for use in oligonucleotide synthetic regimes. Representative phosphoryl protecting groups are the 2-cyanoethyl (see U.S. Pat. Nos. 4,725,677 and Re. 34,069 to Koster et al.), methyl, 4-cyano-2-butenyl, and diphenylmethylsilylethyl (DPSE) groups.

The phosphoryl protecting group is typically bound to the phosphoryl group to be protected by the addition of a reagent of formula HO—$R_5$ and with the release of a diaklylamino, morpholino, or similar amino group, to form a support-bound phosphite having the formula:

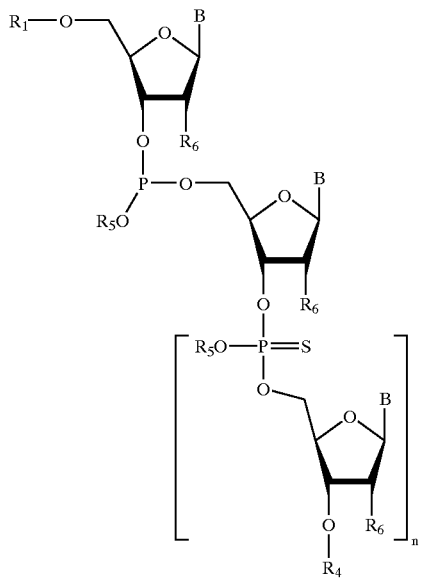

The group —$OR_5$ is preferably attached to the phosphorus in the presence of an activating agent, which is preferably an organic base such as tetrazole. The support-bound phosphite is then sulfurized, and then deprotected at the 5'-position to form a further support-bound synthon where n is increased by 1. The cycle is repeated in iterative fashion until the desired phosphorothioate is achieved. The completed oligonucleotide phosphorothioate is then cleaved from the solid support, typically with a strong base such as ammonium hydroxide. During cleavage, the phosphorus protecting groups are cleaved as well as the link to the solid support. Thus, the cleavage step, which can precede or follow deprotection of protected functional groups, will yield a phosphorothioate free of all protecting groups.

Sulfurizing agents used during oxidation to form phosphorothioate linkages include Beaucage reagent (see e.g. Iyer, R. P., et.al., *J. Chem. Soc.*, 1990, 112, 1253–1254, and Iyer, R. P., et.al., *J. Org. Chem.*, 1990, 55, 4693–4699); tetraethylthiuram disulfide (see e.g., Vu, H., Hirschbein, B. L., *Tetrahedron Lett.*, 1991, 32, 3005–3008); dibenzoyl tetrasulfide (see e.g., Rao, M. V., et.al., *Tetrahedron Lett.*, 1992, 33, 4839–4842); di(phenylacetyl)disulfide (see e.g., Kamer, P. C. J., *Tetrahedron Lett.*, 1989, 30, 6757–6760); 1,2,4-dithiuazoline-5-one (DtsNH) and 3-ethoxy-1,2,4-dithiuazoline-5-one (EDITH) and (see Xu et al., *Nucleic Acids Research*, 1996, 24, 3643–3644 and Xu et al., *Nucleic Acids Research*, 1996, 24, 1602–1607); thiophosphorus compounds such as those disclosed in U.S. Pat. No. 5,292,875 to Stec et al., and U.S. Pat. No. 5,151,510 to Stec et al., disulfides of sulfonic acids, such as those disclosed in Efimov et al., *Nucleic Acids Research*, 1995, 23, 4029–4033, sulfur, sulfur in combination with ligands like triaryl, trialkyl, triaralkyl, or trialkaryl phosphines.

In the context of the present invention, the term "oligonucleotide" refers to a plurality of joined nucleotide units formed in a specific sequence. The term nucleotide has its accustomed meaning as the phosphoryl ester of a nucleoside. The term "nucleoside" also has its accustomed meaning as a pentofuranosyl sugar which is bound to a nucleosidic base (i.e, a nitrogenous heterocyclic base or "nucleobase").

The methods of the present invention can be used for the synthesis of phosphorothioate oligomers having both naturally occurring and non-naturally occurring constituent groups. For example, the present invention can be used to synthesize phosphorothioate oligomers having naturally occurring pentose sugar components such as ribose and deoxyribose, and their substituted derivatives, as well as other sugars known to substitute therefor in oligonucleotide analogs.

The methods of the invention are used for the preparation of phosphorothioate oligonucleotides. The constituent sugars and nucleosidic bases of the phosphorothioate oligonucleotides can be naturally occurring or non-naturally occurring. Non-naturally occurring sugars and nucleosidic bases are typically structurally distinguishable from, yet functionally interchangeable with, naturally occurring sugars (e.g. ribose and deoxyribose) and nucleosidic bases (e.g., adenine, guanine, cytosine, thymine). Thus, non-naturally occurring nucleobases and sugars include all such structures which mimic the structure and/or function of naturally occurring species, and which aid in the binding of the phosphorothioate to a target, or which otherwise advantageously contribute to the properties of the phosphorothioate oligomer.

The methods of the invention are amenable to the synthesis of phoshorothioate oligomers having a variety of substituents attached to their 2'-positions. These include, for example, halogens, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, the disclosure of which is hereby incorporated by reference.

Sugars having O-substitutions on the ribosyl ring are also amenable to the present invention. Representative substitutions for ring O include S, $CH_2$, CHF, and $CF_2$, see, e.g., Secrist, et al., *Abstract 21, Program & Abstracts, Tenth International Roundtable, Nucleosides, Nucleotides and their Biological Applications*, Park City, Utah, Sep. 16–20, 1992.

Representative nucleobases suitable for use in the methods of the invention include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoro-methyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, P. D., *Anti-Cancer Drug Design*, 1991, 6, 585–607. The terms "nucleosidic base" and "nucleobase" are further intended to include heterocyclic compounds that can serve as nucleosidic bases, including certain 'universal bases' that are not nucleosidic bases in the most classical sense, but function similarly to nucleosidic bases. One representative example of such a universal base is 3-nitropyrrole.

The methods of the present invention use labile protecting groups to protect various functional moieties during synthesis. Protecting groups are used in the oligonucleotide synthetic methods of the invention for protection of several different types of functionality. In general, protecting groups render chemical functionality inert to specific reaction conditions and can be appended to and removed from such functionality in a molecule without substantially damaging the remainder of the molecule. See, e.g., Green and Wuts, Protective Groups in Organic Synthesis, 2d edition, John Wiley & Sons, New York, 1991. Representative hydroxyl protecting groups used for nucleic acid chemistry are described by Beaucage, et al., *Tetrahedron* 1992, 48, 2223. Representative protecting groups useful to protect nucleotides during phosphorothioate synthesis include base labile protecting groups and acid labile protecting groups. Base labile protecting groups are used to protect the exocyclic amino groups of the heterocyclic nucleobases. This type of protection is generally achieved by acylation. Two commonly used acylating groups are benzoylchloride and isobutyrylchloride. These protecting groups are stable to the reaction conditions used during oligonucleotide synthesis and are cleaved at approximately equal rates during the base treatment at the end of synthesis. The second type of protection used in the phosphorothioate synthetic methods of the invention is an acid labile protecting group, which is used to protect the nucleotide 5' hydroxyl during synthesis.

The amino moiety of the phosphordiamidites of the invention can be selected from various amines presently used for phosphoramidites in standard oligonucleotide synthesis. These include both aliphatic and heteroalkyl amines. One preferred amino group is diisopropylamino. Other examples of suitable amines as are described in various United States patents, principally those to M. Caruthers and associates. These include U.S. Pat. Nos. 4,668,777; 4,458,066; 4,415,732; and 4,500,707; all of which are herein incorporated by reference.

In some preferred embodiments of the invention the phosphordiamidite is activated to nucleophilic attack by the 5' hydroxyl by use of an activating agent. It is believed that the activating agent displaces one of the amino groups from the phosphordiamidite, thereby rendering the phosphorus of the phosphordiamidite more susceptible to nucleophilic attack by the 5' hydroxyl group of the growing nucleotide chain. Any activating agent that can activate the phosphorous to nucleophilic attack without interacting with the growing nucleotide chain may be suitable for use with the present invention. One preferred activating agent is tetrazole. Some commonly used commercially available activating agents are thiotetrazole, nitrotetrazole, and N,N-diisopropylaminohydrotetrazolide. Other suitable activating agents are also disclosed in the above incorporated patents as well as in U.S. Pat. No. 4,725,677 and in Berner, S., Muhlegger, K., and Seliger, H., *Nucleic Acids Research* 1989, 17:853; Dahl, B. H., Nielsen, J. and Dahl, O., *Nucleic Acids Research* 1987, 15:1729; and Nielson, J. Marugg, J. E., Van Boom, J. H., Honnens, J., Taagaard, M. and Dahl, O., *J. Chem. Research* 1986, 26, all of which are herein incorporated by reference.

It is generally preferable to perform a capping step, either prior to or after sulfurization of the support-bound phosphite. Such a capping step is generally known to provide benefits in the prevention of shortened oligomer chains, by blocking chains that have not reacted in the coupling cycle. One representative reagent used for capping is acetic anhydride. Other suitable capping reagents and methodologies can be found in U.S. Pat. No. 4,816,571.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

As used herein, the term O-alkylamino denotes a group of formula O-alkyl-$NH_2$. The term O-alkylalkoxy denotes a group of formula —O-alkyl-O-alkyl. The term O-alkylaminoalkyl denotes an O-alkylamino group wherein the amino moiety bears one or more additional alkyl groups. The The term O-akylimidazole means a group of formula O-alkyl-imidazole.

As used herein, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments of the invention $R_4$ is a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y, 1991, Chapter 1, pages 1–23.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527), Tenta-Gel Support (an aminopolyethyleneglycol derivatized support (see, e.g., Wright, et al., *Tetrahedron Letters* 1993, 34, 3373)) and Poros (a copolymer of polystyrene/divinylbenzene).

In some preferred embodiments of the invention $R_1$ or $R_4$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, supra, at Chapter 2. Preferred protecting groups used for $R_2$, $R_3$ and $R_{3a}$ include dimethoxytrityl (DMT), monomethoxytrityl, 9-phenylxanthen-9-yl (Pixyl) and 9-(p-methoxyphenyl)xanthen-9-yl (Mox). The $R_2$ or $R_3$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or other groups, such as, for example, 2'-alkoxy groups (e.g., where $R_1$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Phosphorothioates produced by the methods of the invention will preferably be hybridizable to a specific target oligonucleotide. Preferably, the phosphorothioates produced by the methods of the invention comprise from about 1 to about 100 monomer subunits. It is more preferred that such compounds comprise from about 10 to about 30 monomer subunits, with 15 to 25 monomer subunits being particularly preferred.

In one aspect of the invention, the compounds of the invention are used to modulate RNA or DNA, which code for a protein whose formation or activity it is desired to modulate. The targeting portion of the composition to be employed is, thus, selected to be complementary to the preselected portion of DNA or RNA, that is to be hybridizable to that portion.

The oligomeric compounds of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

Additional advantages and novel features of this invention will become apparent to those skilled in the art upon examination of the examples thereof provided below, which should not be construed as limiting the appended claims.

EXAMPLE 1

Preparation of 5'-O-dimethoxytrityl-base protected nucleoside 3'-O-phosphorbismorpholidites These compounds were synthesized according to the procedure of Uznanski, B. et al., *Tetrahedron Letters*, 1987, 28, 3401–3404.

EXAMPLE 2

Preparation of 5'-O-dimethoxytrityl-base protected nucleoside 3'-O-phosphorbisdiethylamidites These compounds were synthesized according to the procedure of Yamana, K. et al., *Tetrahedron*, 1989, 45, 4135–4140.

EXAMPLE 3

Synthesis of T-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of 5'-O-(4,4'-dimethoxytrityl)thymidine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 3-hydroxypropionitrile in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/

THF (1:1:8), and N-methyl imidazole/THF is added to cap the unallowed to 5'-hydroxyl group. The product is washed with acetonitrile.

The carrier containing the compound is treated with 30% aqueous ammonium hydroxide solution for 90 minutes. The aqueous solution is filtered, and concentrated under reduced pressure to give a phosphorothioate dimer of T-T.

EXAMPLE 4

Synthesis of dC-T phosphorothioate dimer 100 milligrams (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. A 0.2 M solution of $N^4$-benzoyl-5'-O-(4,4'-dimethoxytrityl)-2'-deoxycytidine-3'-O-phosphorbismorpholidite in acetonitrile and a 0.4 M solution of 1H-tetrazole in acetonitrile are added, and allowed to react at room temperature for 5 minutes. The product is washed with acetonitrile, and then a 0.8M solution of 3-hydroxypropionitrile in acetonitrile and a 0.4 M solution of 1H-tetrazole in acetonitrile are added and allowed to react at room temperature for 5 minutes. The product is washed with acetonitrile, and this step is repeated one more time. The product is then washed with acetonitrile, and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dC-T.

EXAMPLE 5

Synthesis of dG-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyguanosine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 3-hydroxypropionitrile in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dG-T.

EXAMPLE 6

Synthesis of dA-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyadenosine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 3-hydroxypropionitrile in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dA-T.

EXAMPLE 7

Synthesis of T-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of 5'-O-(4,4'-dimethoxytrityl)thymidine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 2-diphenylmethylsilylethanol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes. The aqueous solution is filtered, concentrated under reduced pressure to give a phosphorothioate dimer of T-T.

EXAMPLE 8
Synthesis of dC-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^4$-benzoyl-5'-O-(4,4'-dimethoxytrityl)-2'-deoxycytidine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 2-diphenylmethylsilylethanol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dC-T.

EXAMPLE 9
Synthesis of dG-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyguanosine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 2-diphenylmethylsilylethanol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the any unreacted 5'-hydroxyl groups to 5'-hydroxyl group. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dG-T.

EXAMPLE 10
Synthesis of dA-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyadenosine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 2-diphenylmethylsilylethanol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dA-T.

EXAMPLE 11
Synthesis of T-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of 5'-O-(4,4'-dimethoxytrityl)thymidine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes. The aqueous solution is filtered, concentrated under reduced pressure to give a phosphorothioate dimer of T-T.

EXAMPLE 12

Synthesis of dC-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group The product is washed with dichloromethane and then with acetonitrile. Then, a 0.2 M solution of $N^4$-benzoyl-5'-O-(4,4'-dimethoxytrityl)-2'-deoxycytidine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dC-T.

EXAMPLE 13

Synthesis of dG-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyguanosine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dG-T.

EXAMPLE 14

Synthesis of dA-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyadenosine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dA-T.

EXAMPLE 15

Synthesis of T-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of 5'-O-(4,4'-dimethoxytrityl)thymidine-3'-O-phosphorbismorpholidite in acetonitrile and a 0.4 M solution of 1H-tetrazole in acetonitrile is added, and allowed to react at room temperature for 5 minutes. The product is washed with acetonitrile, and then a 0.8M solution of 3-hydroxypropionitrile in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes. The aqueous solution is filtered, concentrated under reduced pressure to give a phosphorothioate dimer of T-T.

EXAMPLE 16

Synthesis of C-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^4$-benzoyl-5'-O-(4,4'-dimethoxytrityl)-2'-deoxycytidine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 3-hydroxypropionitrile in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dC-T.

EXAMPLE 17

Synthesis of dG-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyguanosine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 3-hydroxypropionitrile in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dG-T.

EXAMPLE 18

Synthesis of dA-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyadenosine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 3-hydroxypropionitrile in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dA-T.

EXAMPLE 19

Synthesis of T-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of 5'-O-(4,4'-dimethoxytrityl)thymidine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 2-diphenylmethylsilylethanol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes. The aqueous solution is filtered, concentrated under reduced pressure to give a phosphorothioate dimer of T-T.

EXAMPLE 20

Synthesis of dC-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^4$-benzoyl-5'-O-(4,4'-dimethoxytrityl)-2'-deoxycytidine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 2-diphenylmethylsilylethanol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dC-T.

EXAMPLE 21

Synthesis of dG-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyguanosine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 2-diphenylmethylsilylethanol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dG-T.

EXAMPLE 22

Synthesis of dA-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyadenosine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 2-diphenylmethylsilylethanol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dA-T.

EXAMPLE 23

Synthesis of T-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of 5'-O-(4,4'-dimethoxytrityl)thymidine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes. The aqueous solution is filtered, concentrated under reduced pressure to give a phosphorothioate dimer of T-T.

EXAMPLE 24

Synthesis of dC-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^4$-benzoyl-5'-O-(4,4'-dimethoxytrityl)-2'-deoxycytidine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dC-T.

EXAMPLE 25

Synthesis of dG-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of $N^2$-isobutyryl-5'-O-(4,4'-dimethoxytrityl)-2'-deoxyguanosine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dG-T.

EXAMPLE 26

Synthesis of dA-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5-hydroxyl group. The product is washed with dichloromethane and then with acetonitrile. Then, a 0.2 M solution of $N^2$-isobutyryl-5'-O-(4,4'-dimethoxytrityl)-2'-deoxyadenosine-3'-O-phosphorbisethylamidite in acetonitrile and a 0.4 M solution of 1H-tetrazole in acetonitrile is added, and allowed to react at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile and this step is repeated one more time. Then the product is washed with acetonitrile and a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dA-T.

EXAMPLE 27

Synthesis of 5'-TTTTTTT-3' phosphorothioate heptamer 50 milligram (2 mmole) of 5'-O-Dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2 M solution of 5'-O-(4,4'-dimethoxytrityl)thymidine-3'-O-phosphorbisethylamidite in acetonitrile and a 0.4 M solution of 1H-tetrazole in acetonitrile is added, and allowed to at room-temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile, and this step is repeated one more time. Then a 0.05 M solution of Beaucage reagent in acetonitrile is added and allowed to at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

This complete cycle is repeated five more times to get the completely protected thymidine heptamer. The carrier containing the compound is treated with 30% aqueous ammonium hydroxide solution for 90 minutes at room temperature. The aqueous solution is filtered, concentrated under reduced pressure to give a phosphorothioate heptamer of TTTTTTT.

EXAMPLE 28

Synthesis of 5'-d(GACT)-3' phosphorothioate tetramer 50 milligram (2 mmole) of 5'-O-Dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2 M solution of 5'-O-(4,4'-dimethoxytrityl)thymidine-3'-O-phosphorbisethylamidite in acetonitrile and a 0.4 M solution of 1H-tetrazole in acetonitrile is added, and allowed to at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile, and this step is repeated one more time. The product is washed with acetonitrile, and then a 0.05 M solution of Beaucage reagent in acetonitrile is added and allowed to at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

A dichloromethane solution of 2% dichloroacetic acid (volume/volume) is added to deprotect the 5'-hydroxyl group. The product is washed with acetonitrile. Then, a 0.2 M solution of $N^4$-benzoyl-5'-O-(4,4'-dimethoxytrityl)-2'-deoxycytidine-3'-O-phosphorbisethylamidite in acetonitrile and a 0.4 M solution of 1H-tetrazole in acetonitrile is added, and allowed to at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile, and this step is repeated one more time. The product is washed with acetonitrile, and then a 0.05 M solution of Beaucage reagent in acetonitrile is added and allowed to at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

A dichloromethane solution of 2% dichloroacetic acid (volume/volume) is added to deprotect the 5'-hydroxyl group. The product is washed with acetonitrile. Then, a 0.2 M solution of $N^6$-benzoyl-5'-O-(4,4'-dimethoxytrityl)-2'-deoxyadenosine-3'-O-phosphorbisethylamidite in anhydrous acetonitrile and a 0.4 M solution of 1H-tetrazole in acetonitrile is added, and allowed to at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile, and this step is repeated one more time. The product is washed with acetonitrile, and then a 0.05 M solution of Beaucage reagent in acetonitrile is added and allowed to at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

A dichloromethane solution of 2% dichloroacetic acid (volume/volume) is added to deprotect the 5'-hydroxyl group. The product is washed with acetonitrile. Then, a 0.2 M solution of $N^2$-isobutyryl-5'-O-(4,4'-dimethoxytrityl)-2'-deoxyguanosine-3'-O-phosphorbisethylamidite in acetonitrile and a 0.4 M solution of 1H-tetrazole in acetonitrile is added, and allowed to at room temperature for 5 minutes. The product is washed with acetonitrile, and then a 0.8M solution of 4-cyano-2-butene-1-ol in acetonitrile and a 0.4 M solution of 1H-tetrazole in acetonitrile are added and allowed to react at room temperature for 5 minutes. The product is washed with acetonitrile, and this step is repeated one more time. The product is washed with acetonitrile, and then a 0.05 M solution of Beaucage reagent in acetonitrile is added and allowed to at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

The carrier containing the compound is treated with 30% aqueous ammonium hydroxide solution for 90 minutes at room temperature and then incubated at 55° C. for 24 hour. The aqueous solution is filtered, concentrated under reduced pressure to give a phosphorothioate tetramer of 5'-dG-dA-dC-T-3'.

It is intended that each of the patents, applications, and printed publications mentioned or referred to in this specification be herein incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound of formula:

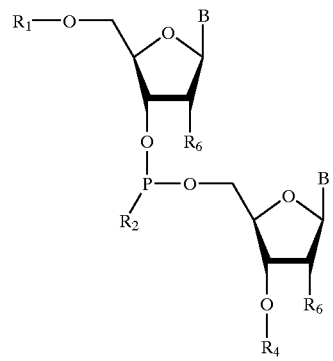

wherein:

B is a nucleosidic base;

$R_1$ is a protecting group;

$R_2$ is dialkylamino or morpholino;

$R_4$ is a linker connected to a solid support; and $R_6$ is halogen, O-alkyl, O-alkylamino, O-alkylalkoxy, protected O-alkylamino, O-alkylaminoalkyl, O-alkyl imidazole, or a polyether of the formula (O-alkyl)$_m$, where m is 1 to about 10.

2. The compound of claim 1, wherein $R_2$ is diisopropylamino.

3. The compound of claim 1, wherein $R_2$ is morpholino.

4. The compound of claim 1, wherein the phosphoryl protecting group is cyanoethyl.

5. The compound of claim 1, wherein the phosphoryl protecting group is 4-cyano-2-butenyl.

6. The compound of claim 1, wherein the phosphoryl protecting group is diphenylmethylsilylethyl.

7. The compound of claim 1, wherein $R_6$ is a polyether of the formula $(O\text{-alkyl})_m$, where m is 1 to about 10.

* * * * *